Figure 1:
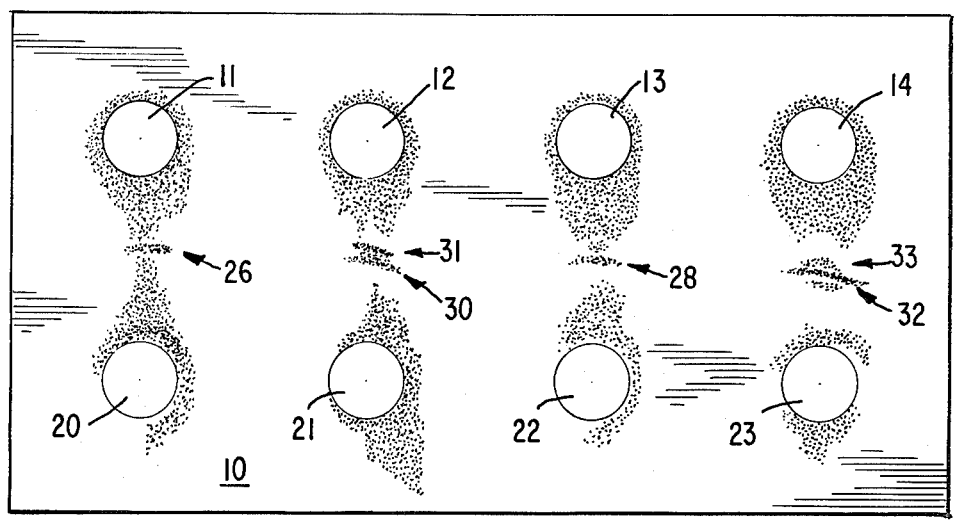

United States Patent [19]

Wilson et al.

[11] 4,322,274

[45] Mar. 30, 1982

[54] METHOD OF DIAGNOSING CYSTIC FIBROSIS PATIENTS AND ASYMPTOMATIC CARRIER OF THE CYSTIC FIBROSIS GENE

[76] Inventors: Gregory B. Wilson, 2706 Cameron Blvd.; H. Hugh Fudenberg, 9 Second Ave., both of Isle of Palms, S.C. 29451

[21] Appl. No.: 182,007
[22] Filed: Aug. 28, 1980
[51] Int. Cl.³ .................... G01N 27/26; G01N 33/16
[52] U.S. Cl. ........................ 204/180 G; 204/299 R; 23/230 B; 23/902; 424/12; 424/85; 424/177
[58] Field of Search ...................... 204/180 G, 180 S; 424/12, 85, 177; 23/230 B, 902

[56] References Cited

U.S. PATENT DOCUMENTS

| | | | |
|---|---|---|---|
| 3,674,678 | 7/1972 | Post, Jr. et al. | 204/180 G X |
| 3,736,100 | 5/1973 | Rains | 204/180 G X |
| 3,912,610 | 10/1975 | Lou | 204/180 G |
| 4,097,149 | 6/1978 | Aladjem et al. | 204/180 G X |
| 4,198,389 | 4/1980 | Wadsworth | 204/180 G |

OTHER PUBLICATIONS

Manson and Brock, "Development of a Quantitative Immunoassay for the Cystic Fibrosis Gene", *The Lancet*, Feb. 16, 1980, pp. 330 and 331.
Gregory B. Wilson, "Cystic Fibrosis Protein, a Confirmed Diagnostic Marker for Detecting Heterozygote Carriers: Significance in Relation to Future Screening and to a Proposed Primary Defect in Alpha$_2$-Macroglobulin", *Pediatrics Research*, Sep., 1979, vol. 13, pp. 1079-1081.
Wilson and Fudenberg, "Letter to the Editor: Is Cystic Fibrosis Protein a Diagnostic Marker for Individuals Who Harbor the Defective Gene?", *Pediatrics Research* vol. 12, (1978), pp. 801-804.
Wilson and Fudenberg, "Separation of ciliary dyskinesia substances found in serum and secreted by cystic fibrosis leukocytes and lymphoid cell lines, using protein A–Sepharose CL-4B", *Journal of Laboratory and Clinical Medicine*, (1978), vol. 92, pp. 463-482.
Wilson et al. "Demonstration of Serum Protein Differences in Cystic Fibrosis by Isoelectric Focusing in Thin-Layer Polyacrylamide Gels", *Clinical Chimica Acta*, vol. 49, (1973) pp. 79-91.
Wilson and Fudenberg, "Studies on Cystic Fibrosis Using Isoelectric Focusing. I. An Assay for Detection of Cystic Fibrosis Hemozygotes and Heterozygote Carriers from Serum", *Pediatrics Research*, vol. 9 (1975) pp. 635-640.
Wilson et al., "Improved Method for Detection of Cystic Fibrosis Protein in Serum Using the LKB Multiphor Electrofocusing Apparatus", *Pediatric Research*, vol. 11, (1977) pp. 986-989.
Wilson et al., "Additional Notes on the Use of Analytic Isoelectric Focusing for the Detection of Cystic Fibrosis Protein in Serum", *Peditrics Research*, vol. 11, (1977), pp. 139-141.
Wilson et al., "Studies on Cystic Fibrosis Using Isoelectric Focusing .III. Correlation Between Cystic Fibrosis Protein and Ciliary Dyskinesia Activity in Serum Shown by a Modified Rabbit Tracheal Bioassay", *Pediatrics Research*, vol. 11 (1977) pp. 143-146.
Wilson et al., "Letter to the Editor: Detection of Cystic Fibrosis Protein by Electrofocusing", *Pediatrics Research*, vol. 10 (1976), pp. 1001-1002.

*Primary Examiner*—Arthur C. Prescott
*Attorney, Agent, or Firm*—Garrettson Ellis

[57] ABSTRACT

An immunologic method has been devised enabling diagnosis of patients with cystic fibrosis, as well as asymptomatic carriers of the cystic fibrosis gene. Monospecific antibody to Cystic Fibrosis Protein (CFP) is inserted into a first position on an electrophoresis plate. A body fluid from the subject to be tested is placed into a second position on the plate. An electrical potential is imposed across the positions with the anode being adjacent to the section containing the serum and the cathode being adjacent to the section containing the antibody. The presence of Cystic Fibrosis Protein is indicated by one or more precipitation zones forming where the body fluid proteins meet the antibody due to movement induced by an applied electrical potential. The relative position of the precipitation zone between the first and second positions, or the area of the precipitation zone, indicates a concentration of the Cystic Fibrosis Protein. Methods for producing the purified Cystic Fibrosis Protein antibody and for purifying the Cystic Fibrosis Protein itself are also disclosed.

31 Claims, 2 Drawing Figures

METHOD OF DIAGNOSING CYSTIC FIBROSIS PATIENTS AND ASYMPTOMATIC CARRIER OF THE CYSTIC FIBROSIS GENE

BACKGROUND OF THE INVENTION

In our article in *Pediatric Research*, Volume 12, pages 801–804 (1978), we discussed the possibility that individuals who possess two defective genes causing them to be victims of cystic fibrosis, or asymptomatic genetic carriers having one abnormal gene produce a unique protein termed "Cystic Fibrosis Protein" (CEP). This CFP can be isolated using isoelectric focusing in thin layer polyacrylamide gels as described in the publication by Wilson, Jahn and Fonesca, *Clin. Chim. Acta*, Volume 49, page 79 (1973); G. B. Wilson et al. *Pediatric Research*, 9:635 (1975); and G. B. Wilson et al. *Pediatric Research*, 11:986 (1977). The Cystic Fibrosis Protein is characterized as a protein with an isoelectric point (pI) of $8.46 \pm 0.05$, and is found in more than 90 percent of individuals tested who are homozygous and heterozygous for the cystic fibrosis gene. However, the Cystic Fibrosis Protein is absent from 92 percent of normal control subjects tested under standardized and controlled conditions.

In accordance with this invention, a method is provided for diagnosing cystic fibrosis in patients and also diagnosing asymptomatic carriers of the cystic fibrosis gene, based upon the detection of Cystic Fibrosis Protein in the blood plasma or serum of patients. Frequently it has been found that the test of this invention can distinguish between those actively suffering from cystic fibrosis and asymptomatic carriers by the concentration of Cystic Fibrosis Protein present in the serum, as determined by the method of this invention.

Furthermore, it is preferred in the method of this invention to utilize a monospecific antibody to Cystic Fibrosis Protein. Methods are described herein for obtaining antibody to Cystic Fibrosis Protein and particularly highly purified, monospecific antibody formulations.

DESCRIPTION OF THE INVENTION

In accordance with this invention, a method is provided for diagnosing cystic fibrosis in patients and also for diagnosing asymptomatic carriers of the cystic fibrosis gene. The method comprises inserting monospecific antibody to Cystic Fibrosis Protein into a first position on a gel-covered plate. A body fluid for diagnosis is inserted into a second position on the plate. An electric potential is imposed across the positions, with the anode being positioned adjacent to the position containing the body fluid, and the cathode is adjacent to the section containing the monospecific antibody.

The presence of Cystic Fibrosis Protein, which is the indicator of the presence of the cystic fibrosis gene, is indicated by at least one precipitation zone, with the relative position of the precipitation zone between the first and second positions or the area of the zone indicating the concentration of the Cystic Fibrosis Protein.

Cystic Fibrosis Protein antibody from hyperimmune mouse sera produces a pair of lines of precipitation against serum of Cystic Fibrosis homozygotes and obligate heterzygote carriers, and only a single line against normal control sera when analyzed by known counterimmunoelectrophoresis or immunoelectrophoresis techniques.

The hyperimmune mouse sera used above may be further purified of unwanted antibodies by the addition of sufficient amounts of human serum or immunoglobulin G (IgG), free of Cystic Fibrosis Protein, to remove the unwanted antibodies. Under this circumstance of use of a substantially pure antibody a single precipitation zone is formed in the electrophoresis process between the first and second positions described above, while no precipitation zone is obtained in the presence of a control serum free of Cystic Fibrosis Protein.

In addition, the precipitation zone obtained by a counterimmunoelectrophoresis technique against the serum of obligate heterozygote carriers is usually closer to the second position on the electrophoresis plate and fainter than the line obtained against the serum of cystic fibrosis homozygotes, indicating the presence of less Cystic Fibrosis Protein. Thus, this test, which may be done rapidly and utilizes reduced amounts of antiserum compared with other tests, can be used not only to diagnose cystic fibrosis, but additionally to identify asymptomatic carriers in many cases. Alternatively, Laurell rocket immunoelectrophoresis may be used. The method may employ incorporating the antibody in a gel section and the CFP in slots near the anode. The applied potential causes electrophoresis of the CFP into the antibody-containing gel so that precipitation zones or "rockets" of conical shape are formed. The height of the rocket is proportional to the concentration of the CFP in the sample.

The monospecific antibody CFP also allows quantification of CFP levels in serum and can be employed to diagnose cystic fibrosis and locate asymptomatic carriers in many cases.

Monospecific CFP antibody may be also used in other diagnostic techniques for the detection of Cystic Fibrosis Protein including direct or indirect radioimmunoassay, enzyme-linked solid or liquid phase immunoassay or passive hemagglutinationassay with antibody-coated cells or single or double immunodiffusion techniques, for example.

The body fluid for diagnosis utilized herein may be amniotic fluid for diagnosis of CFP in a fetus, blood serum, saliva, urine or a tissue culture supernatant, among others.

The Cystic Fibrosis Protein needed for the above methods may be purified in the following manner:

The serum of individuals possessing the defective gene causing cystic fibrosis may be incubated with protein A from *Staphylococcus auereus*, covalently coupled to a solid carrier, particularly Sepharose and specifically Sepharose CL-4B, to specifically absorb the immunoglobulin G and materials bound thereto. It is of course considered to be an equivalent technique within the scope of this invention to pass various components of serum of individuals possessing the defective gene, or modified serum, as long as the specific step of the absorption of the immunoglobulin G to the bound protein A takes place.

Thereafter the protein A and carrier, with its absorbed immunoglobulin G, is placed into an aqueous solution buffered to acidic pH, preferably pH 2.5–3.5 such as pH 3.0, to dissociate Cystic Fibrosis Protein and immunoglobulin G from the protein A.

After this, isoelectric focusing of the dissociated Cystic Fibrosis Protein and IgG may take place on a gel surface, so that the Cystic Fibrosis Protein is largely isolated at a certain area on the gel. Alternatively, the protein A-IgG-CFP complexes may be placed directly on a gel near the anode to be electrofocused. Specific techniques that may be utilized in the isoelectric or electrofocusing technique are as described in the following articles:

Wilson, Arnaud and Fudenberg, Improved Method for the Detection of Cystic Fibrosis Protein in Serum Using the LKB Multiphor Focusing Apparatus, *Pediatric Research*, Volume 11, page 986 (1977); Wilson, Arnaud, Monsher and Fudenberg, Detection of Cystic Fibrosis Protein by Electrofocusing, *Pediatric Research*, Volume 10, page 1001 (1976); Wilson, Monsher and Fudenberg, Additional Notes on the Use of Analytic Isoelectric Focusing for the Detection of Cystic Fibrosis Protein in Serum, *Pediatric Research*, Volume 11, page 139 (1977); Wilson, Fudenberg and Jahn, Studies on Cystic Fibrosis Using Isoelectric Focusing. I. An Assay for the Detection of Cystic Fibrosis Homozygotes and Heterozygote Carriers from Serum, *Pediatric Research*, Volume 9, page 635 (1975).

Specifically, a pH gradient of about 2.5 to 10 or preferably 5–10 may be used, and a potential of at least about 1000 V up to about 1500 V, although higher or lower potentials may be used depending on the time allowed for electrofocusing.

After the electrofocusing technique, fixation and staining of the gel may also be accomplished using tricholoracetic acid and sulfosalicylic acid at 4° C. before staining, or concurrently fixed and stained at 80° C. employing both of the above acids as described in the article of Wilson, Fudenberg, and Jahn in *Pediatric Research*, Volume 9, page 635 (1975) or the article by Wilson, Arnaud and Fudenberg in *Pediatric Research*, Volume 11, page 986 (1977).

The resulting isoelectrically focused Cystic Fibrosis Protein on the gel is a protein band with a pI between pH 8.4 and 8.5, located in a specific position on the gel surface.

Fixation and staining of the gel is normally carried out using a small section of the gel to insure that proper focusing of the CFP has occurred. Following this, a first portion of the focused (unfixed and unstained) gel which contains the purified Cystic Fibrosis Protein is excised, and emulsified in a saline solution of physiological concentration.

Alternatively the CFP can be purified from IgG either after the acidification of the protein A gel-IgG-CFP mixture or after emulsification of the electrofused gel containing CFP, by chromatography on a gel column of for example Bio-gel P-10 (sold by Bio-rad). The pure CFP may then be coupled covalently to a carrier such as methylated Bovine Serum albumin for injection.

Thereafter, the emulsified saline mixture is injected into a target animal, such as goat, sheep, rabbit, horse, or mouse. Preferably, the target animal is a new-born mouse which has been previously immunized at birth with a saline emulsion of a second excised portion of isoelectrically focused gel derived from the serum of a cystic fibrosis free-donor, with the second excised portion of electrofocused gel being from the gel portion that the Cystic Fibrosis Protein would have occupied if present, and otherwise corresponding to the first excised gel portion containing Cystic Fibrosis Protein. The effect of this is to cause the new-born mouse to become tolerant to the material found in the second excised portion of the electrofocused gel in the sense that it fails to form antibodies to such materials upon subsequent immunological challenge.

The mouse is thus immunized with the emulsion of the first electrofocused gel portion containing the Cystic Fibrosis Protein, with the result that the mouse, in an appropriate period of time, produces a monospecific antibody for Cystic Fibrosis Protein which is uncontaminated with any antibodies for the other materials found in the first and second portions of the electrofocused gel.

The antibody produced by the mouse or other target animal may be then collected and isolated by conventional techniques and used. Specifically, the antibody may also be purified by reaction with normal human plasma or immunoglobulin G, to neutralize extraneous antibodies to purify the antibody for the Cystic Fibrosis Protein.

However, preferably, hybridoma clones may be prepared by fusing spleen cells from the mouse or other immune target animal with nonimmunoglobulin secreting cells, such as murine myeloma cells. The resulting fused cells (hybrids) are then isolated by known techniques, and may be cultured to produce preferably monospecific antibody for Cystic Fibrosis Protein.

Figure 2:
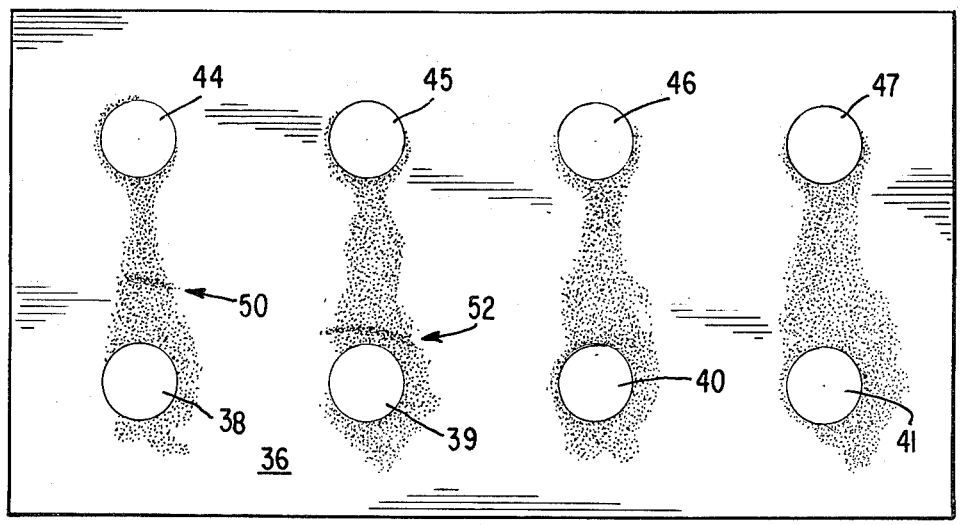

Referring to the drawings, FIG. 1 and FIG. 2 each are plan view of counterimmunoelectrophoresis plates, coated with gel and used for detection of CFP in accordance with this invention.

Specific examples of the manufacture of a test kit using counterimmunoelectrophoresis in accordance with this invention are described below. It is understood that the specific examples described below are for illustrative purposes only, and are not intended to limit the scope of the invention of this application, which is as defined in the claims below.

As described in our article in the *Journal of Laboratory and Clinical Medicine*, Volume 92, No. 3, pages 463–482 (September, 1978), protein A purified from *S. aureus* and covalently coupled to an insoluble matrix of Sepharose CL-4B by the cyanogen bromide method was purchased from Pharmacia Fine Chemicals, Piscataway, N.J. The protein A content of the gel was reported to be 2 mg. per ml. of gel, and the binding capacity was indicated to be approximately 25 mg. of immunoglobulin G per ml. of gel.

Prior to use, various amounts of the dry gel were weighed out, suspended in phosphate buffered saline at pH 7.2 in 5 ml. of the phosphate buffered saline per 10 mg. of dry gel, and incubated at 37° C. for 90 minutes, to allow the gel to swell. The cell was then resuspended and washed three times in phosphate buffered saline at pH 7.2 maintaining a gel-to-liquid ratio of 1:10 by volume, to remove dextran and lactose added by the manufacturer. The gel suspension was centrifuged at 250 g. for 15 minutes after each wash to recover the solids.

Cell-free serum from a cystic fibrosis patient was added to the protein A-Sepharose gel in a quantity sufficient to provide approximately 25 mg. of immunoglobulin G per ml. of gel. The mixture was incubated for 60 minutes at 37° C. with constant agitation to keep the gel in suspension. After incubation, the tubes were centrifuged at 250 g. for 15 minutes, and the protein A gel was collected.

The resulting filter residue was washed with the phosphate buffered saline solution described above. Thereafter, the protein A-Sepharose carrier gel and absorbed immunoglobulin G was placed into an aqueous solution buffered to pH 3.0, to dissociate the Cystic Fibrosis Protein and immunoglobulin G from protein A. Following centrifugation to separate the solids from the liquids, the liquid residue constituted a suspension of the Cystic Fibrosis Protein and IgG with other serum components such as kallikrein and plasmin removed by the process. These components in particular can interfere with the purification of the Cystic Fibrosis Protein since they have isoelectric points (pI) close to that of Cystic Fibrosis Protein.

The Cystic Fibrosis Protein was further purified then by electrofocusing the above suspension on a polyacrylamide gel surface by means of a technique as specifically described in the references cited above using a gradient of a range of at least 5 pH units in the range of pH 2.5–10, including pH 8 to 9 and a potential of about 1000 volts, and 35 watts, including a current of preferably 1 to 100 milliampere. The area of the electrofocused gel surface which contained proteins having a pI of 8.46±0.05, constituting purified Cystic Fibrosis Protein (and small amounts of IgG) was then excised with a sharp knife and emulsified in isotonic acetate buffer at pH 3.5–5.5 and typically pH 4.7. The acidic pH insures that the Cystic Fibrosis Protein remains dissociated from immunoglobulin G when injected. Specifically, the pH of such a solution should be less than 6 and preferably less than 5, but as stated, the solution must be physiological, i.e., not capable of causing injury to the recipient, since it is intended for injection into a target animal.

The physiological emulsified solution was then used to immunize BALB/c mice intraperitoneally weekly for three to six weeks.

Serum was then collected from the mice and placed on the agarose (agar) gel-coated electrophoresis plate of FIG. 1, identified by reference numeral 10, with the hyperimmune mouse sera being placed in upper wells 11 to 14.

Serum from patients having cystic fibrosis was placed in lower wells 21 and 23. Serum from normal patients, free of Cystic Fibrosis Protein, was placed in wells 20 and 22. A 40 MA current was placed in the gel in conventional manner by normal electrodes between wells 11 through 14 and wells 20 through 23, with the anode being adjacent wells 20 through 23 and the cathode being adjacent wells 11 through 14.

As shown in FIG. 1, in the area between wells 11 and 20, and 13 and 22, representing the interaction of normal serum, a single precipitation line 26, 28 is respectively observed. However, between wells 12 and 21, and 14 and 23, double precipitation lines 30 through 33 are observed, providing an indication of the presence of Cystic Fibrosis Protein.

Accordingly, with a supply of purified Cystic Fibrosis Protein antibody obtained as described herein, an easily usable test kit may be provided for screening of potential patients for the diagnosis of cystic fibrosis (neonatal diagnosis), and also for determining carriers of cystic fibrosis gene since the method also detects CFP in their body fluids, and also prenatal diagnosis through amniocentesis.

Referring to FIG. 2, the hyperimmune mouse antisera produced in the manner as described above may be mixed with human sera or immunoglobulin G which is free of Cystic Fibrosis Protein, to remove unwanted antibodies from the hyperimmune mouse serum. The resulting hyperimmune mouse serum may be utilized in conjunction with a conventional agarose (agar) gel-coated electrophoresis plate 36, with the monospecific mouse antisera placed in upper wells 44 through 46. A human serum for test is placed in lower wells 38 through 41. In lower well 38, serum from a cystic fibrosis patient is placed. In lower well 39 the serum from a symptom-free obligate heterozygote carrier of cystic fibrosis is placed. Normal human serum is placed in lower wells 40 and 41. Following counterimmunoelectrophoresis of conventional type (as described in Oudin and Williams, Precipitation Analysis by Diffusion in Gels, found in: Williams and Chase, *Methods in Immunology and Immunochemistry*, Volume III, pages 103–374, Academic Press, New York and London (1973)) under the priordescribed conditions, with the anode being adjacent wells 38 through 41, a single precipitation line 50 forms between wells 44 and 38, confirming the cystic fibrosis diagnosis of that particular plasma donor.

Between wells 39 and 45, another precipitation line 52 is formed, but the line tends to be fainter, and is closer to well 39, which indicates a reduced concentration of Cystic Fibrosis Protein, consistent with the identification of a symptom-free carrier of the cystic fibrosis gene.

With respect to wells 40, 46, and 41, 47, no precipitation line is shown, confirming the fact that these donors are free of the cystic fibrosis gene.

As a further modification of this invention, hybridoma clones may be prepared by fusing spleen cells from the mice immunized as described above with non-immunoglobulin-secreting murine myeloma cells (for example, line S194/S-XXO Bu. 1) employing standard techniques such as described in the article by Kohler and Milstein, Continuous Cultures of Fused Cells Secreting Antibody of Predefined Specificity, *Nature* (1975), Volume 256, pages 495–496; and the article by Vaughan, Hansen, and Stadler, Parameters of Polyethylene Glycol-Induced Cell Fusion and Hybridization in Lymphoid Cell Lines, *Somatic Cell Genet.* (1976), Volume 2, pages 537–544.

The fused cells may then be utilized in conventional manner to produce monospecific antibody in quantity. To get a pure culture of the hybridoma cells, they may be grown in a special media such as Hat F-12 by Littlefield, which selectively kills unfused tumor cells over a period of a few weeks, while the desired hybridoma cells survive for longer periods of time, producing monospecific antibody which may be harvested and used in the testing method described above.

That which is claimed is:

1. The method which comprises producing monospecific anitbody to Cystic Fibrosis Protein; inserting said monospecific antibody to Cystic Fibrosis Protein into a first position on a gel-coated electrophoresis plate; inserting a body fluid for diagnosing into a second position on said plate; imposing an electric potential across said position, with an electrode being adjacent said body fluid and the opposite pole electrode being adjacent the antibody, the presence of Cystic Fibrosis Protein being indicated by at least one precipitation zone, the relative position of said precipitation zone between the first and second positions indicating the concentration of Cystic Fibrosis Protein.

2. The method of claim 1 in which the monospecific antibody is prepared by injecting a newborn animal with protein impurities found in a specific Cystic Fibrosis Protein dispersion to cause the newborn mouse to become tolerant of said protein impurities, and thereafter immunizing said mouse with the Cystic Fibrosis Protein dispersion, whereby monospecific antibody for Cystic Fibrosis Protein is produced and thereafter isolating said antibody for use on the gel-coated electrophoresis plate.

3. The method of diagnosing cystic fibrosis in patients, and also diagnosing asymptomatic carriers of the cystic fibrosis gene, which comprises:
   inserting monospecific antibody to Cystic Fibrosis Protein into a first position on a gel-coated electrophoresis plate, said monospecific antibody having been purified of other antibodies by treatment with a material selected from the group consisting of serum and isolated components from serum;
   inserting a body fluid for diagnosing into a second position on said plate;
   imposing an electric potential across said positions, with an electrode being adjacent said body fluid and the opposite pole electrode being adjacent the antibody, the presence of Cystic Fibrosis Protein being indicated by at least one precipitation zone, the relative position of said precipitation zone between the first and second positions indicating the concentration of Cystic Fibrosis Protein.

4. The method of claim 3 in which said monospecific anitbody is derived from mouse antiserum.

5. The method of claim 4 in which the anode is adjacent the body fluid and the cathode is adjacent the antibody.

6. The method of claim 5 in which said gel is selected from the group consisting of agar and agarose.

7. The method of claim 6 in which a DC electric current of at least 1 to 100 MA is applied between said anode and cathode.

8. The method of producing antibody to Cystic Fibrosis Protein, which comprises:
   incubating a source of impure Cystic Fibrosis Protein from individuals possessing the defective gene causing cystic fibrosis with protein A from *Staphylococcus auereus* covalently coupled to a solid carrier, to specifically absorb IgG and materials bound to the IgG; placing said protein A-carrier and absorbed IgG into an aqueous solution; dissociating Cystic Fibrosis Protein and the IgG from protein A; effecting isoelectric focusing of the resulting solution containing Cystic Fibrosis Protein on a gel; excising a first portion of the focused gel which contains purified Cystic Fibrosis Protein, and dispersing at least the CFP from said focused gel in a physiological solution; injecting said solution into a target animal; and obtaining Cystic Fibrosis Protein antibody from said target animal.

9. The method of claim 8 in which said dissociation is caused by use of an acidic buffered aqueous solution.

10. The method of claim 2 in which said acidic solution is buffered at pH 2.5–3.5.

11. The method of claim 8 including the step of preparing hybridoma clones by fusing spleen cells from immune target animals with nonimmunoglobulin-secreting murine myeloma cells, and isolating the resulting cells which produce antibody for Cystic Fibrosis Protein.

12. The method of claim 8 in which said carrier is Sepharose.

13. The method of claim 8 in which said target animal is a mouse.

14. The method of claim 8 in which said first portion of the focused gel is emulsified in a physiological acetate buffer solution of a pH of 3.5 to 5.5.

15. The method of claim 8 in which said target animal is a newborn mouse which has been immunized with at least the Cystic Fibrosis Protein from a second excised portion of isoelectrically focused gel derived from the serum of a cystic fibrosis-free donor, said excised portion of focused gel otherwise corresponding to said first excised portion containing Cystic Fibrosis Protein, to cause the newborn mouse to become tolerant of the materials found in the second excised portion of electrofocused gel and thereafter immunizing said mouse with said emulsion of the first electrofocused gel, whereby the antibody for Cystic Fibrosis Protein produced is monospecific.

16. The method of claim 8 in which said antibody for Cystic Fibrosis Protein is rendered monospecific by treatment with a material selected from the group consisting of Cystic Fibrosis Protein-free human serum and components thereof to inactivate all other antibodies.

17. The method of claim 8 in which said isoelectric focusing is performed at a pH gradient of a range of at least 5 pH units, including pH 8 to 9, and a DC electric potential of at least 1000–2000 volts.

18. The method of claim 8 in which the first portion of the focused gel is at pI 8.4 to 8.5.

19. The method of claim 8 in which the first portion of focused gel is emulsified in a physiological solution prior to injection into the target animal.

20. The method of claim 15 in which the first portion of the focused gel is at pI 8.4 to 8.5.

21. The method of claim 15 in which the first portion of focused gel is emulsified in a physiological solution prior to injection into the target animal.

22. The method of producing antibody to Cystic Fibrosis Protein which comprises:
   incubating a body fluid of individuals possessing the defective gene causing cystic fibrosis through a protein A from *Staphylococcus auereus* covalently coupled to a solid support, to specifically absorb IgG and materials bound to the IgG;
   placing said solid supported protein A and absorbed IgG into an acidic-buffered aqueous solution to dissociate Cystic Fibrosis Protein from the IgG and both IgG and CFP from protein A;
   effecting isoelectric focusing of the resulting solution containing Cystic Fibrosis Protein on a gel across a pH gradient including pH 8 to 9 and at least 1000 volts potential;
   removing the portion of the focused gel at pI 8.4 to 8.5 which contains purified Cystic Fibrosis Protein, and emulsifying said focused gel in a buffered solution of physiological concentration and acid pH;
   injecting said emulsified solution into a target animal;
   allowing the target animal to become immune;
   preparing hybridoma clones by fusing spleen cells from said immune target animal with nonimmunoglobulin-secreting murine myeloma cells, and isolating the resulting cells which produce antibody for Cystic Fibrosis Protein; and
   isolating said Cystic Fibrosis Protein using antibody made by such cells.

23. The method of claim 22 in which said solid suppot is Sepharose.

24. The method of claim 22 in which said portion of the focused gel is emulsified in a physiological acetate buffer solution of a pH of 3.5 to 5.5.

25. The method of claim 22 in which said target animal is a mouse.

26. The method of claim 22 in which said target animal if a new-born mouse which has been immunized with an emulsion of a second excised portion of isoelectrically focused gel at pI 8.4 to 8.5 derived from the serum of a cystic fibrosis-free donor, said excised portion of focused gel otherwise corresponding to the orginal excised portion containing Cystic Fibrosis Protein, to cause the new-born mouse to become tolerant of the materials found in the second excised portion of electrofocused gel and thereafter immunizing said mouse with said emulsion of the first electrofocused gel, whereby the antibody for Cystic Fibrosis Protein produced is monospecific.

27. The method of claim 21 in which said isoelectric focusing is performed at a pH gradient of a range of at least 5 pH units, including pH 8 to 9, and a DC electric potential of at least 1000 volts.

28. The method of producing antibody to Cystic Fibrosis Protein, which comprises:
incubating a source of impure Cystic Fibrosis Protein from individuals possessing the defective gene causing cystic fibrosis with protein A from *Staphylococcus auereus* covalently coupled to a solid carrier, to specifically absorb IgG and materials bound to the IgG; placing said protein A-carrier and absorbed IgG into an aqueous solution; dissociating Cystic Fibrosis Protein and the IgG from Protein A; effecting isoelectric focusing of the resulting solution containing Cystic Fibrosis Protein on a gel; excising a first portion of the of the focused gel which contains purified Cystic Fibrosis Protein, and dispersing at least the Cystic Fibrosis Protein from said focused gel in a physiological solution; injecting said solution into a target animal; preparing hybridroma clones by fusing spleen cells from immune target animals with nonimmunoglobulin-secreting murine myeloma cells, isolating and culturing the resulting cells which produce antibody for Cystic Fibrosis Protein and purifying the Cystic Fibrosis Protein so obtained.

29. The method of claim 28 in which said target animal is a newborn mouse which has been immunized with at least the Cystic Fibrosis Protein from a second excised portion of isoelectrically focused gel derived from the serum of a cystic fibrosis-free donor, said excised portion of focused gel otherwise corresponding to said first excised portion containing Cystic Fibrosis Protein, to cause the newborn mouse to become tolerant of the materials found in the second excised portion of electrofused gel and thereafter immunizing said mouse with said emulsion of the first electrofocused gel, whereby the anibody for Cystic Fibrosis Protein produced is monospecific.

30. The method of claim 28 in which said antibody for Cystic Fibrosis Protein is rendered monospecific by treatment with a material selected from the group consisting of Cystic Fibrosis Protein-free human serum and components thereof to inactivate all other antibodies allowing the target animal to become immune.

31. The method of claim 28 in which said isoelectric focusing is performed at a pH gradient of a range of at least 5 pH units, including pH 8 to 9, and a DC electric potential of at least 1000–2000 volts.

* * * * *